US011499958B2

(12) United States Patent
Nakaya et al.

(10) Patent No.: US 11,499,958 B2
(45) Date of Patent: Nov. 15, 2022

(54) BIOLOGICAL TISSUE ANALYZING DEVICE, BIOLOGICAL TISSUE ANALYZING PROGRAM, AND BIOLOGICAL TISSUE ANALYZING METHOD

(71) Applicant: Daiki Nakaya, Tokyo (JP)

(72) Inventors: Daiki Nakaya, Tokyo (JP); Shin Satori, Chiba (JP)

(73) Assignee: Daiki Nakaya, Tokyo (JP)

( * ) Notice: Subject to any disclaimer, the term of this patent is extended or adjusted under 35 U.S.C. 154(b) by 0 days.

(21) Appl. No.: 16/981,451

(22) PCT Filed: Mar. 18, 2019

(86) PCT No.: PCT/JP2019/011152
§ 371 (c)(1),
(2) Date: Sep. 16, 2020

(87) PCT Pub. No.: WO2019/181845
PCT Pub. Date: Sep. 26, 2019

(65) Prior Publication Data
US 2021/0072219 A1    Mar. 11, 2021

(30) Foreign Application Priority Data

Mar. 19, 2018  (JP) .............................. JP2018-051114

(51) Int. Cl.
*G01N 21/27*    (2006.01)
*G01N 33/483*   (2006.01)
*G01N 21/64*    (2006.01)

(52) U.S. Cl.
CPC ......... *G01N 33/4833* (2013.01); *G01N 21/27* (2013.01); *G01N 21/6486* (2013.01)

(58) Field of Classification Search
CPC .. G01N 33/4833; G01N 33/574; G01N 21/27; G01N 2021/6491; G01J 3/2823; G01J 2003/2826
See application file for complete search history.

(56) References Cited

U.S. PATENT DOCUMENTS

2002/0146160 A1 * 10/2002 Parker .................. G06T 11/206
                                                                  382/131
2006/0074835 A1    4/2006 Maggioni
(Continued)

FOREIGN PATENT DOCUMENTS

| EP | 2133023 A1 | 12/2009 |
| JP | 2017-203637 A | 11/2017 |
| WO | WO2018160963 | * 9/2018 ............... A61B 5/00 |

OTHER PUBLICATIONS

Kiyotoki Shu et al, New method for detection of gastric cancer by hyperspectral imaging: a pilot study, Journal of biomedical Optics, vol. 18(2), Feb. 2013, p. 026010.

*Primary Examiner* — Maurice C Smith
(74) *Attorney, Agent, or Firm* — Muncy, Geissler, Olds & Lowe, P.C.

(57) ABSTRACT

A biological tissue analyzing device configured to analyze a biological tissue using hyperspectral data in which spectral information is associated with each of pixels forming a two-dimensional image and comprising the following (i) and (ii), as well as comprising (iii) and/or (iv):
(i) a hyperspectral data acquisition unit configured to acquire the hyperspectral data;
(ii) an analysis target region extraction unit configured to extract pixels corresponding to an analysis target region from a two-dimensional image of the biological tissue;
(iii) an altered state classification unit configured to roughly classify an altered state of the biological tissue with unsupervised learning; and
(Continued)

(iv) an altered state identification unit configured to identify the altered state of the biological tissue with supervised learning.

16 Claims, 9 Drawing Sheets

(56) References Cited

U.S. PATENT DOCUMENTS

| | | | |
|---|---|---|---|
| 2013/0338479 A1* | 12/2013 | Pogue | G16H 30/40 600/408 |
| 2015/0119721 A1* | 4/2015 | Pedersen | G06T 7/0012 600/476 |
| 2017/0154420 A1* | 6/2017 | Barnes | G06T 5/003 |
| 2018/0005085 A1* | 1/2018 | Kakileti | G06K 9/6267 |
| 2018/0247153 A1* | 8/2018 | Ganapati | A61B 1/005 |
| 2019/0261913 A1* | 8/2019 | Beaulieu | A61B 5/7275 |
| 2019/0279362 A1* | 9/2019 | Marrero Callico | G06K 9/00 |

* cited by examiner

[Fig.1]
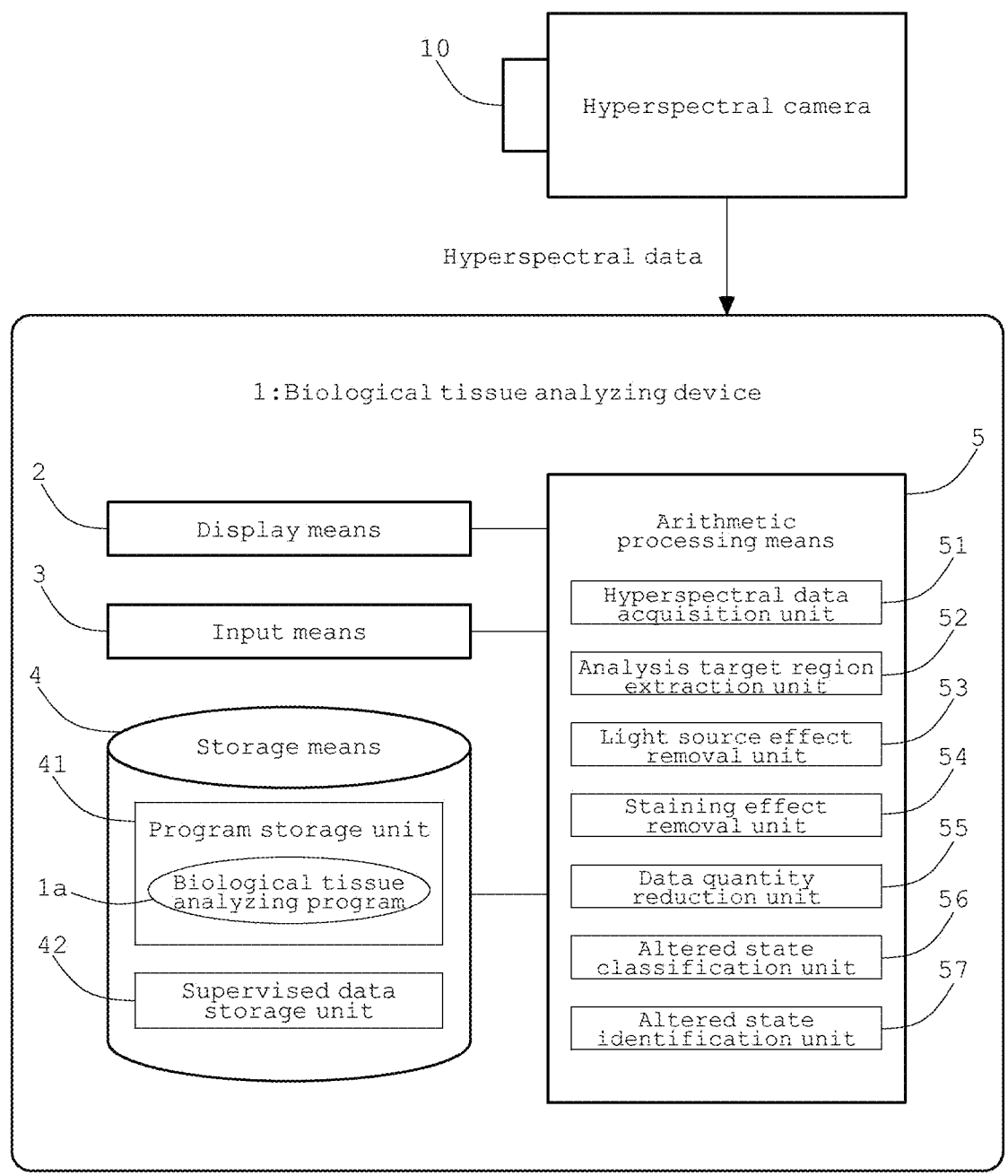

[Fig.2]
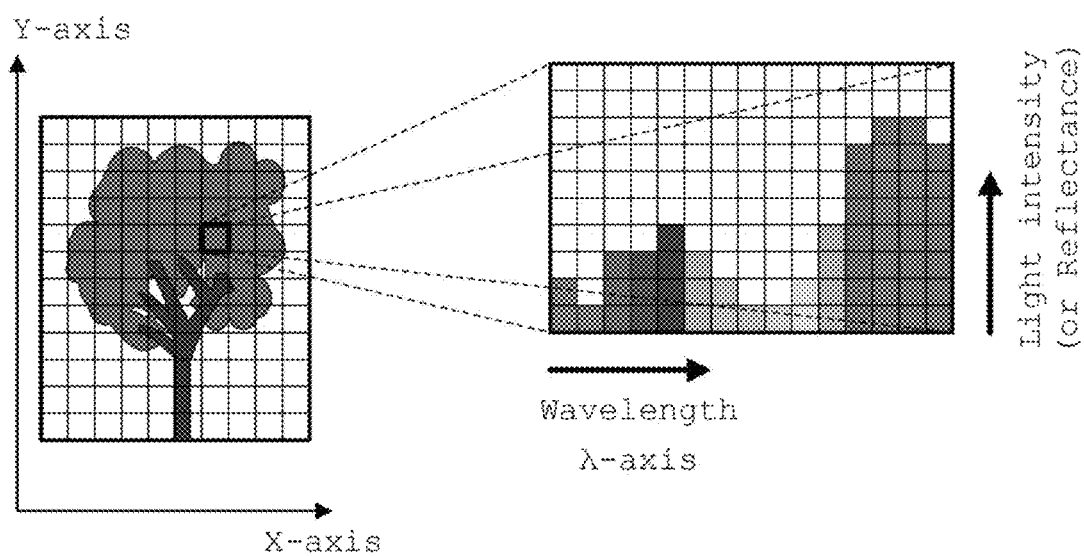
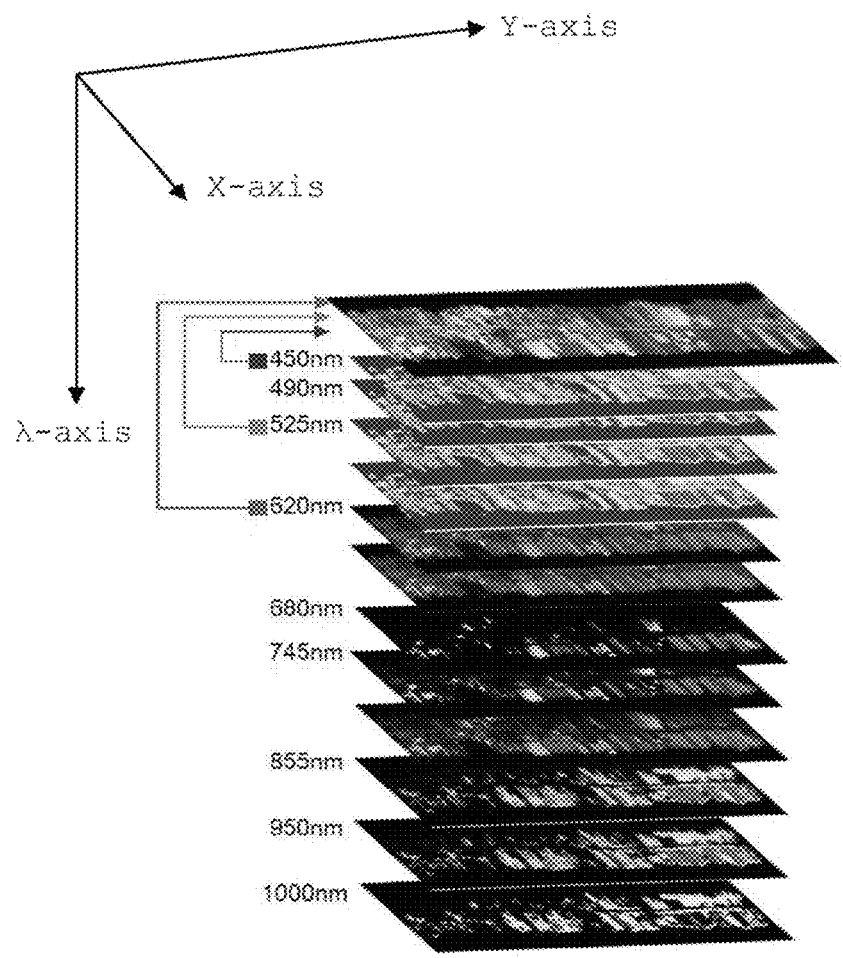

[Fig.3]
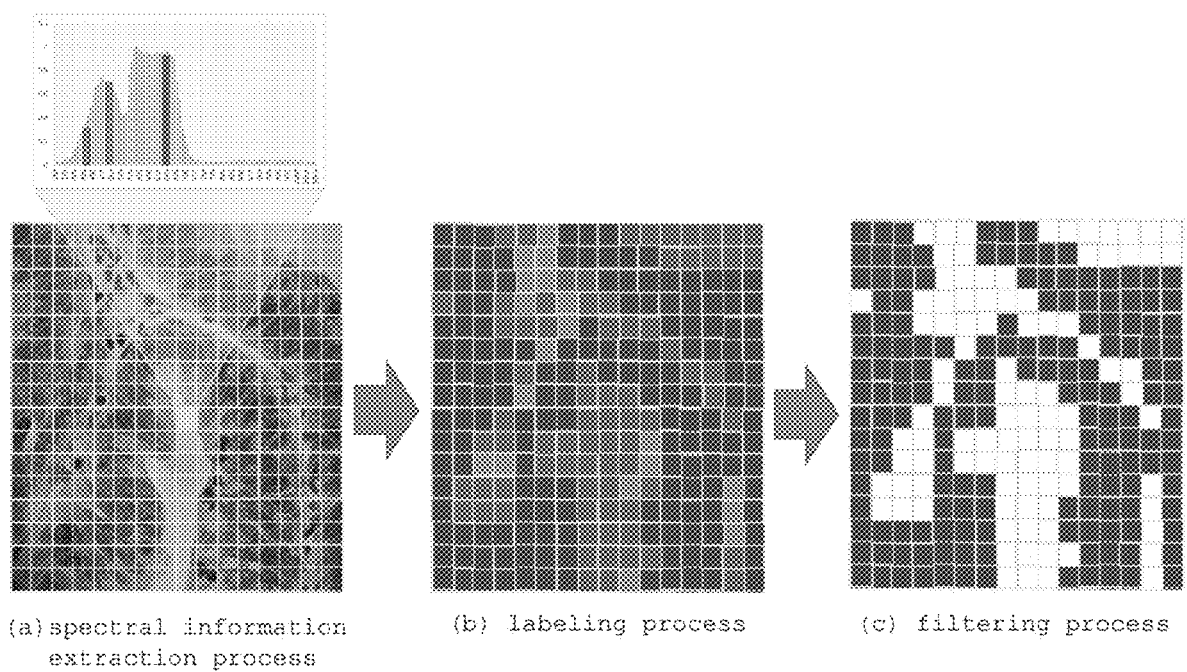
(a) spectral information extraction process
(b) labeling process
(c) filtering process

[Fig.4]
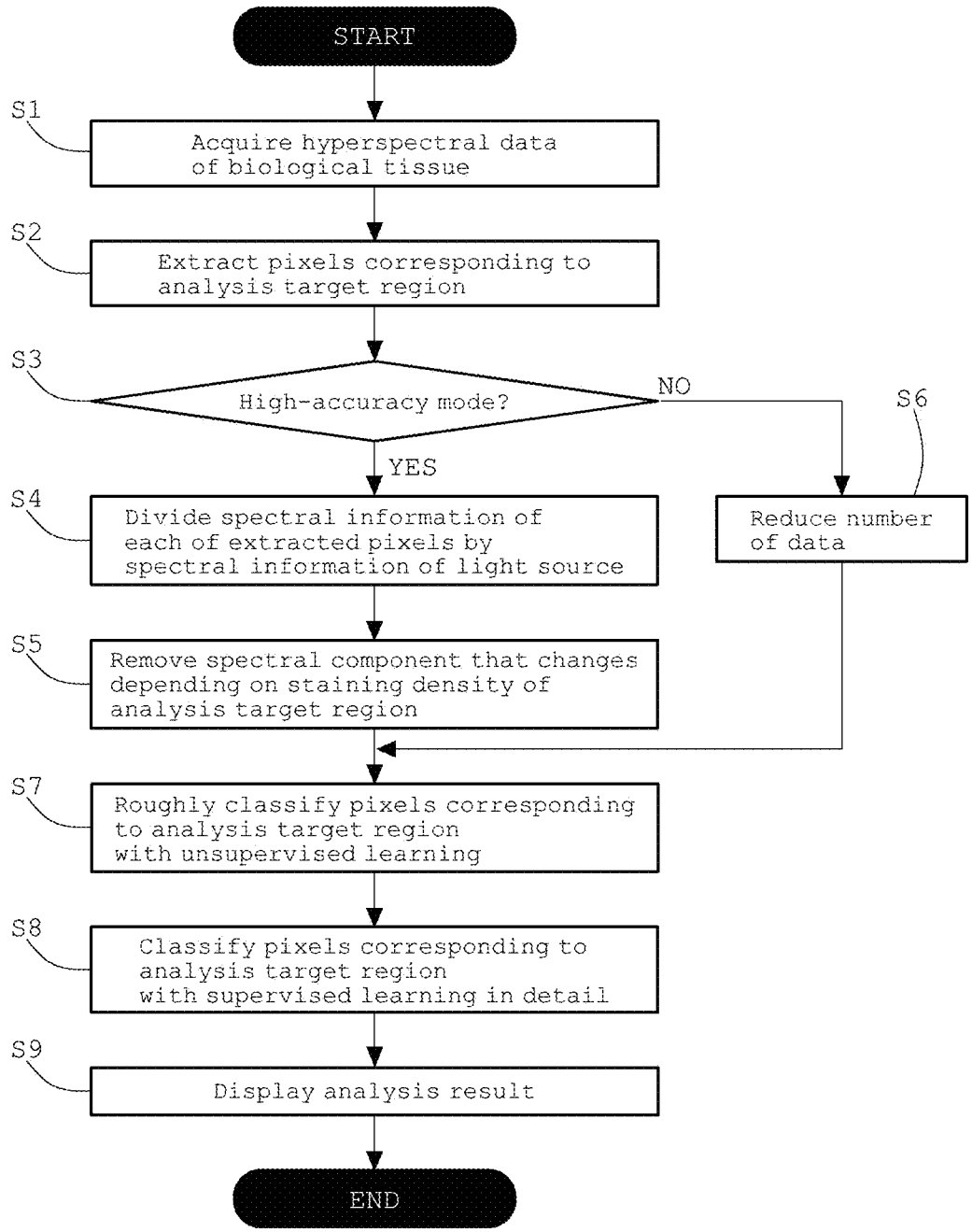

[Fig.5]

| | Cancer | | | HGD | | | LGD | | | | Non-cancer | | | |
|---|---|---|---|---|---|---|---|---|---|---|---|---|---|---|
| | 1 | 2 | 3 | 1 | 2 | 3 | 1 | 2 | 3 | 4 | 1 | 2 | 3 | 4 |
| Cancer1 | | 85 | 82.5 | 60 | 20 | 95 | 92.5 | 40 | 57.5 | 100 | 100 | 95 | 100 | 95 |
| Cancer2 | | | 70 | 80 | 96.7 | 65 | 97.5 | 90 | 50 | 100 | 100 | 100 | 100 | 100 |
| Cancer3 | | | | 80 | 96.7 | 70 | 100 | 95 | 70 | 100 | 100 | 100 | 100 | 100 |
| HGD1 | | | | | 96.7 | 75 | 97.5 | 70 | 62.5 | 100 | 100 | 100 | 100 | 100 |
| HGD2 | | | | | | 96.7 | 83.3 | 70 | 96.7 | 100 | 100 | 100 | 100 | 100 |
| HGD3 | | | | | | | 100 | 92.5 | 70 | 100 | 100 | 100 | 100 | 100 |
| LGD1 | | | | | | | | 95 | 97.5 | 100 | 100 | 100 | 100 | 100 |
| LGD2 | | | | | | | | | 80 | 100 | 100 | 100 | 100 | 100 |
| LGD3 | | | | | | | | | | 100 | 100 | 100 | 100 | 100 |
| LGD4 | | | | | | | | | | | 100 | 100 | 100 | 100 |
| Non-cancer1 | | | | | | | | | | | | 100 | 15.4 | 100 |
| Non-cancer2 | | | | | | | | | | | | | 100 | 87.5 |
| Non-cancer3 | | | | | | | | | | | | | | 95 |
| Non-cancer4 | | | | | | | | | | | | | | |

[Fig.6]
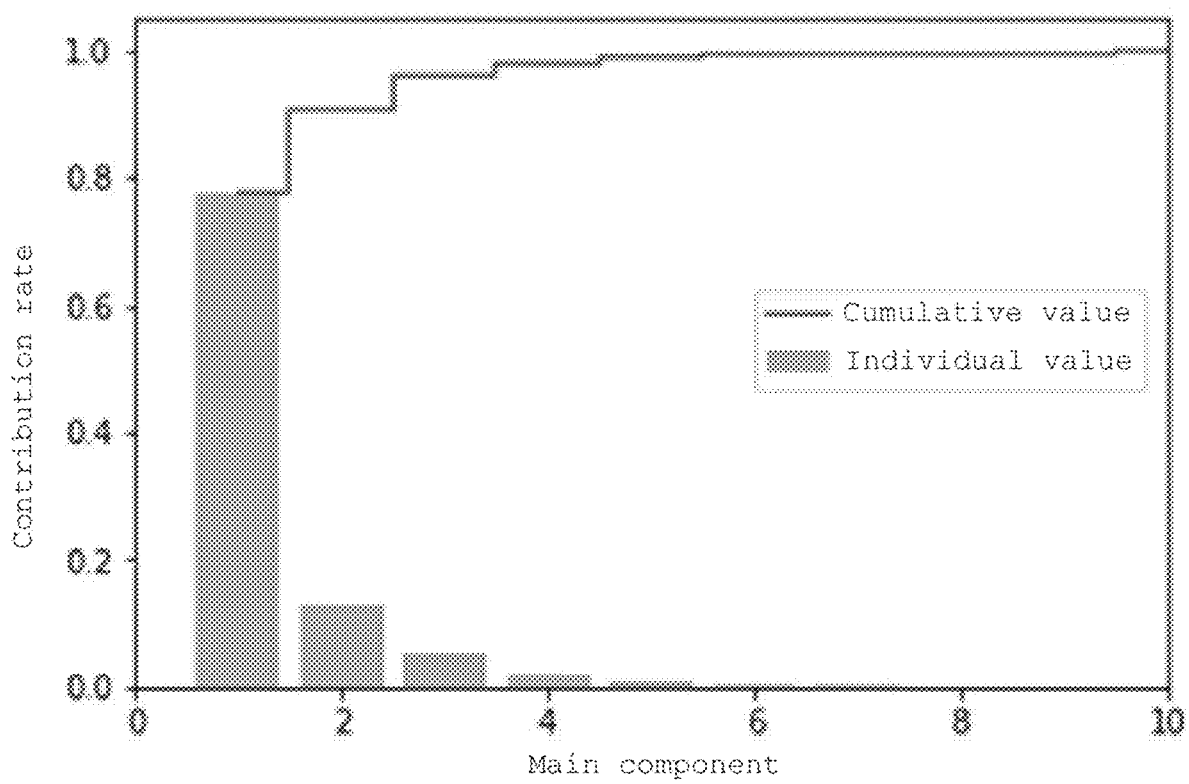

[Fig.7]

|  |  | True result | |
|---|---|---|---|
|  |  | Positive | Negative |
| Prediction result | Positive | 79 | 9 |
|  | Negative | 1 | 154 |

[Fig.8]

(a) Only support vector machine  N=360(90each)

|  |  | Prediction result | | | |
|---|---|---|---|---|---|
|  |  | Cancer | HGD | LGD | Non-cancer |
| Correct answer | Cancer | 83 | 0 | 7 | 0 |
|  | HGD | 14 | 50 | 26 | 0 |
|  | LGD | 10 | 9 | 71 | 0 |
|  | Non-cancer | 0 | 0 | 0 | 90 |

(b) Combination of cluster analysis and support vector machine  N=300(100each)

|  |  | Prediction result | | |
|---|---|---|---|---|
|  |  | Cancer | HGD | LGD |
| Correct answer | Cancer | 90 | 5 | 5 |
|  | HGD | 10 | 71 | 19 |
|  | LGD | 6 | 8 | 86 |

[Fig.9]
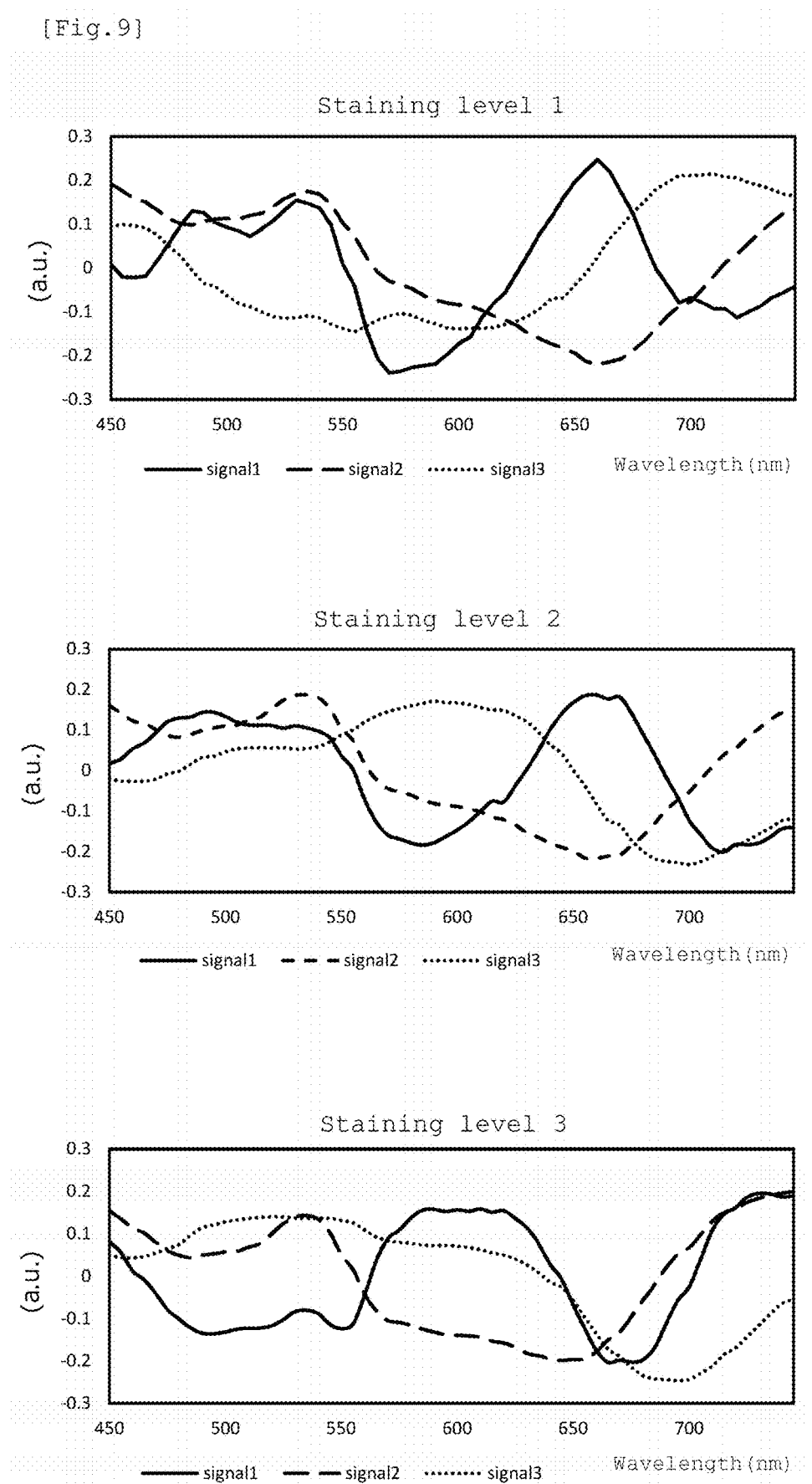

BIOLOGICAL TISSUE ANALYZING DEVICE, BIOLOGICAL TISSUE ANALYZING PROGRAM, AND BIOLOGICAL TISSUE ANALYZING METHOD

TECHNICAL FIELD

The present invention relates to a technique for analyzing a biological tissue using hyperspectral data, and particularly to a biological tissue analyzing device, a biological tissue analyzing program, and a biological tissue analyzing method suitable for identifying an altered state of the biological tissue such as a canceration state of a cell nucleus.

BACKGROUND ART

Conventionally, a pathologist makes a morphological diagnosis using a microscopic image when diagnosing an altered state of a biological tissue such as a canceration state of a cell nucleus. However, such a morphological diagnosis is largely dependent on the knowledge and experience of the pathologist, and the pathologist needs to be trained for several years until becoming a full-fledged expert; hence the morphological diagnosis is difficult.

Therefore, in recent years, a method of optically analyzing a biological tissue using an optical spectrum has been studied. For example, Japanese Patent Laid-Open No. 2017-203637 proposes a method of detecting a tumor cell including an analysis step of determining based on an optical spectrum of a cell contained in a specimen whether such a cell is a tumor cell by a statistical technique, machine learning, or pattern recognition (Patent Literature 1).

CITATION LIST

Patent Literature

Patent Literature 1: Japanese Patent Laid-Open No. 2017-203637

SUMMARY OF INVENTION

Technical Problem

However, the invention disclosed in Patent Literature 1 merely determines whether the cell to be analyzed is a tumor cell. Therefore, there is a problem that altered states of the biological tissue, for example, four stages of canceration states (non-cancer cell, low grade dysplasia (LGD), high grade dysplasia (HGD), and cancer cell) in colon cancer in the early stage of disease can hardly be identified in detail.

The present invention has been made to solve such a problem, and is to provide a biological tissue analyzing device, a biological tissue analyzing program, and a biological tissue analyzing method capable of identifying the altered state of the biological tissue using hyperspectral data with high accuracy.

Solution to Problem

In order to identify the altered state of the biological tissue using the hyperspectral data with high accuracy, the present invention is to provide a biological tissue analyzing device configured to analyze a biological tissue using hyperspectral data in which spectral information is associated with each of pixels forming a two-dimensional image and including the following (i) and (ii), as well as including (iii) and/or (iv):

(i) a hyperspectral data acquisition unit configured to acquire the hyperspectral data of the biological tissue from a hyperspectral camera;

(ii) an analysis target region extraction unit configured to extract, based on the hyperspectral data, pixels corresponding to an analysis target region from a two-dimensional image of the biological tissue by image processing;

(iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning.

In order to improve analysis accuracy by roughly classifying the altered state of the biological tissue in advance, as an aspect of the present invention, the biological tissue analyzing device may include an altered state classification unit configured to categorize the pixels corresponding to the analysis target region with unsupervised learning before the identification by the altered state identification unit.

In order to remove an effect of a light source on data for analysis and to improve the analysis accuracy, as an aspect of the present invention, the biological tissue analyzing device may include a light source effect removal unit configured to divide the spectral information of the pixels corresponding to the analysis target region by spectral information of a light source used at the time of acquisition of the hyperspectral data.

In order to remove an effect of staining on the data for analysis and to improve the analysis accuracy, as an aspect of the present invention, the biological tissue analyzing device may include a staining effect removal unit configured to remove a spectral component which changes depending on staining density of the analysis target region, based on the spectral information of the pixels corresponding to the analysis target region.

In order to extract the analysis target region in pixel units, as an aspect of the present invention, the analysis target region extraction unit may label on each of the pixels as the analysis target region or other regions based on similarity of the spectral information, and may perform filtering on the pixel labeled as the analysis target region.

In order to extract the analysis target region in cell nucleus units, as an aspect of the present invention, the analysis target region extraction unit may perform image recognition processing on the two-dimensional image of the biological tissue to specify a glandular duct, and may specify a cell nucleus present on the glandular duct, as an analysis target region, by image recognition processing.

In order to identify the canceration state of the cell nucleus in a ulcer or a polyp according to a pathological diagnosis, as an aspect of the present invention, the altered state specified by the altered state classification unit may be, in an ulcer: two stages of non-cancer cell and low grade dysplasia (LGD); and the altered state identified by the altered state identification unit may be, in the ulcer: four stages of non-cancer cell, low grade dysplasia (LGD), high grade dysplasia (HGD), and cancer cell, or, in a polyp: three stages of low grade adenoma (LGA), high grade adenoma (HGA), and cancer cell.

In order to acquire hyperspectral data suitable for analyzing the altered state of the biological tissue, as an aspect of the present invention, visible light may be included in a wavelength band of the hyperspectral data.

In order to identify the altered state of the biological tissue using the hyperspectral data with high accuracy, the present invention is to provide a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):

(i) a hyperspectral data acquisition unit configured to acquire the hyperspectral data of the biological tissue from a hyperspectral camera;

(ii) an analysis target region extraction unit configured to extract, based on the hyperspectral data, pixels corresponding to an analysis target region from a two-dimensional image of the biological tissue by image processing;

(iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning.

In order to identify the altered state of the biological tissue using the hyperspectral data with high accuracy, the present invention is to provide a biological tissue analyzing method of analyzing a biological tissue using hyperspectral data in which spectral information is associated with each of pixels forming a two-dimensional image and including the following (i) and (ii), as well as including (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue.

Advantageous Effects of Invention

According to the present invention, it is possible to identify an altered state of a biological tissue using hyperspectral data with high accuracy.

BRIEF DESCRIPTION OF DRAWINGS

FIG. 1 is a block diagram showing a biological tissue analyzing device according to an embodiment of the present invention.

FIG. 2 is a view showing an example of hyperspectral data.

FIG. 3 is a view showing (a) a spectral information extraction process, (b) a labeling process, and (c) a filtering process which are executed by an analysis target region extraction unit of the present embodiment.

FIG. 4 is a flowchart showing a biological tissue analyzing method to be executed by the biological tissue analyzing device and the biological tissue analyzing program of the present embodiment.

FIG. 5 is a table showing identification rates for combinations of all feature quantities in each stage in Example 1.

FIG. 6 is a graph showing a contribution rate of each main component specified by main component analysis in Example 2.

FIG. 7 is a table showing a confusion matrix of prediction results by logistic regression in Example 3.

FIG. 8 is a table showing (a) an analysis result only by a support vector machine and (b) an analysis result by a combination of cluster analysis and support vector machine in Example 4.

FIG. 9 is a graph showing an independent component analysis result of hyperspectral data in Example 5.

DESCRIPTION OF EMBODIMENTS

A biological tissue analyzing device, a biological tissue analyzing program, and a biological tissue analyzing method according to an embodiment of the present invention will be described below with reference to the drawings.

As shown in FIG. 1, a biological tissue analyzing system of the present embodiment includes a hyperspectral camera 10 that acquires hyperspectral data of a biological tissue and a biological tissue analyzing device 1 that analyzes an altered state of the biological tissue based on the hyperspectral data acquired by the hyperspectral camera 10. Respective components will be described below.

In the present invention, the biological tissue is a concept including all tissues in a living body of humans or animals in which a plurality of cells are aggregated in a predetermined pattern. In the present invention, the altered state is a concept including all states, such as the degree of progression of cancer and malignancy of cancer, indicating how much the biological tissue is altered.

The hyperspectral camera 10 simultaneously acquires two-dimensional space information and spectral information (hyperspectral information) at a plurality of wavelengths. Specifically, as shown in FIG. 2, hyperspectral data is acquired in which spectral information is associated with each pixel forming a two-dimensional image. The spectral information, which is also called an optical spectrum, indicates a distribution of light intensity for each band (wavelength).

In the embodiment, the unit pixel forming the two-dimensional image is set to a size included in an analysis target region in the biological tissue, and hyperspectral data having a plurality of pixels is acquired for the analysis target region. In the embodiment, when a canceration state (degree of cancer progression) in ulcers or polyps is analyzed, a cell nucleus is regarded as an analysis target region. However, the analysis target region such as lymphocytes, mucus, or histiocytes (leukocytes) can be appropriately selected according to the altered state of the biological tissue to be analyzed.

In the embodiment, the biological tissue is fixed with formalin or the like and is embedded in paraffin or the like to prepare a slice, and the slice is stained with hematoxylin-eosin and then is sandwiched between preparations. Then, transmitted light obtained by irradiation from the visible light source onto the preparations set in the microscope is enlarged, and the transmitted light is measured by the hyperspectral camera 10 brought into contact with the eyepiece.

Infrared rays and ultraviolet rays used in general medical equipment have a lower transparency (optical coding performance) of a microscope lens compared with a visible light range, and are also susceptible to aberrations. In addition, it is known that calcium fluoride used for the microscope lens interferes with the measurement of a weak Raman signal because of emitting fluorescence due to excitation of near-infrared light. On the other hand, visible light has a smaller photon energy and has less influence on the human body than X-rays. Further, it is known that spectroscopic information of the visible light changes under the influence of chromatin concentration in the cell nucleus, and may potentially contain information of not only chromatin but also cellular tissues as in Raman spectroscopy. Therefore, in the embodiment, the visible light source is used so that visible light is included in the wavelength band of the hyperspectral data.

Next, the biological tissue analyzing device 1 is configured by a computer such as a personal computer, and mainly includes a display means 2, an input means 3, a storage means 4, and an arithmetic processing means 5, as shown in FIG. 1. Each component means will be described below in detail.

The display means 2 is configured by a liquid crystal display, and is used to display analysis results obtained by the biological tissue analyzing device 1. The input means 3 is configured by a keyboard and a mouse, and is used to input instructions and selections from a user. In the embodiment, the display means 2 having only the display function and the input means 3 having only the input function are separately used, but a display/input means such as a touch panel having both the display function and the input function may be used without being limited to such a configuration.

The storage means 4 stores various data and also functions as a working area when the arithmetic processing means 5 performs arithmetic processing. In the embodiment, the storage means 4 is configured by a hard disk, a ROM (Read Only Memory), a RAM (Random Access Memory), and a flash memory, and includes a program storage unit 41 and a supervised data storage unit 42 as shown in FIG. 1. The respective component units will be described below in detail.

A biological tissue analyzing program 1a is installed in the program storage unit 41 to control the biological tissue analyzing device 1 of the embodiment. Then, the arithmetic processing means 5 executes the biological tissue analyzing program 1a to cause the computer as the biological tissue analyzing device 1 to function as each of component units to be described below.

The use of the biological tissue analyzing program 1a is not limited to such a configuration described above. For example, the biological tissue analyzing program 1a may be stored in a computer-readable recording medium such as a CD-ROM or a DVD-ROM, and directly read from the recording medium to be executed. In addition, an external server may be used in a cloud computing method or an ASP (Application Service Provider) method.

The supervised data storage unit 42 stores supervised data as spectral information on the biological tissue. In the embodiment, since the cell nucleus of the ulcer is the analysis target region, spectral information is registered as supervised data for each of altered states specified by, in the ulcer: four stages of non-cancer cell, low grade dysplasia (LGD), high grade dysplasia (HGD), and cancer cell.

The supervised data is appropriately selected according to the altered state of the biological tissue to be analyzed without being limited to the above description. For example, in a case of analyzing a canceration state of a cell nucleus in a polyp, spectral information is registered for each of altered states specified by, in the polyp: three stages of low grade adenoma (LGA), high grade adenoma (HGA), and cancer cell.

The arithmetic processing means 5 acquires hyperspectral data from the hyperspectral camera 10 and executes analysis processing of the biological tissue. In the embodiment, the arithmetic processing means 5 is configured by a CPU (Central Processing Unit) to execute the biological tissue analyzing program 1a installed in the storage means 4, thereby functioning as a hyperspectral data acquisition unit 51, an analysis target region extraction unit 52, a light source effect removal unit 53, a staining effect removal unit 54, a data quantity reduction unit 55, an altered state classification unit 56, and an altered state identification unit 57 as shown in FIG. 1. The respective component units will be described below in detail.

The hyperspectral data acquisition unit 51 acquires hyperspectral data of the biological tissue from the hyperspectral camera 10. In the embodiment, the hyperspectral data acquisition unit 51 outputs a control signal to the hyperspectral camera 10 to scan the biological tissue, and acquires an image signal output from an image pickup element as hyperspectral data line by line.

The analysis target region extraction unit 52 extracts, based on the hyperspectral data, pixels corresponding to the analysis target region from the two-dimensional image of the biological tissue by image processing. In the embodiment, first, the analysis target region extraction unit 52 extracts spectral information of each of the pixels forming the two-dimensional image as shown in FIG. 3(a). Next, as shown in FIG. 3(b), based on similarity of the extracted spectral information, the respective pixels are labeled on the analysis target region and other regions (lymphocytes, histiocytes, and mucus). Then, as shown in FIG. 3(c), the pixels labeled as the analysis target region are filtered. The spectral information (light intensity for each band) of each of the filtered pixels serves as data for analysis.

In the embodiment, the analysis target region extraction unit 52 is configured to calculate the similarity of the spectral information based on an inter-vector distance or a Mahalanobis distance etc. In the embodiment, a threshold value of the similarity is set for the analysis target region and for each of other regions, and the pixel having the similarity equal to or higher than any of the threshold values is labeled as a region corresponding to the threshold value.

In the embodiment, the analysis target region extraction unit 52 extracts the analysis target region based on the similarity of the spectral information, but may adopt another extraction method without being limited to such a configuration. Specifically, the ulcer or the polyp has a glandular duct structure, and a cell nucleus (glandular epithelial cell) being the analysis target region is present on the glandular duct. For this reason, in the case of analyzing the canceration state in the ulcer or the polyp as in the embodiment, the analysis target region extraction unit 52 may combine a two-dimensional image (RGB image) of the biological tissue from the hyperspectral data, perform image recognition processing on the two-dimensional image to specify a glandular duct, and specify the cell nucleus present on the glandular duct, as an analysis target region, by image recognition processing.

The light source effect removal unit 53 is configured to remove the effect of a light source on the data for analysis. In the embodiment, the light source effect removal unit 53 divides the spectral information of the pixel corresponding to the analysis target region by spectral information of the light source used at the time of acquisition of the hyperspectral data, thereby removing the effect of the light source.

Specifically, the light source effect removal unit 53 calculates spectral reflectance $R_i$ for each band of the data for analysis by the following formula (1).

$$R_i = I_i / I_0 \quad \text{Formula (1)}$$

Each reference sign represents as follows.
$I_i$: spectral information of an i-th cell nucleus
$I_0$: spectral information of a light source In the embodiment, since the analysis target region extraction unit 52 extracts the pixels corresponding to the analysis target region as described above, the spectral reflectance $R_i$ is calculated for each of the pixels. However, when the analysis target region extraction unit 52 extracts the analysis target regions through the image recognition processing as described above, the spectral reflectance $R_i$ is calculated for each of the analysis target regions. In addition, when conditions of the light source at the time of acquisition of the hyperspectral data are constant, it is not necessary to cause the light source effect removal unit 53 to function, and the spectral information becomes the data for analysis without change.

The staining effect removal unit 54 removes the effect of staining on the analysis target region on the data for analysis. In the embodiment, the staining effect removal unit 54 removes a spectral component which changes depending on staining density of the analysis target region, based on the spectral information of the pixel corresponding to the analysis target region, thereby removing the effect due to staining.

The spectral component which changes depending on the staining density of the analysis target region, is specified in advance by independent component analysis in Example 5 to be described below. Further, when the staining density of the analysis target region is constant, it is not necessary to cause the staining effect removal unit 54 to function, and the spectral information, from which the spectral component has not been removed, becomes the data for analysis without change.

The data quantity reduction unit 55 reduces the number of data for analysis. In the embodiment, the data quantity reduction unit 55 reduces a dimension of the data for analysis through main component analysis, thereby improving an analysis speed. A method of reducing the number of data is not limited to the main component analysis, and the number of data may be reduced by selection of only any band included in the data for analysis. In addition, when analysis accuracy takes priority over the analysis speed, all the data for analysis may be analyzed without causing the data quantity reduction unit 55 to function.

The altered state classification unit 56 categorizes the pixels corresponding to the analysis target region with unsupervised learning, thereby roughly classifying the altered state of the biological tissue. In the embodiment, the altered state classification unit 56 adopts, as unsupervised learning, cluster analysis (Ward method) for agglomerating a group having similar properties from a group having different properties and forming clusters. Therefore, in the case of analyzing the canceration state in the ulcer as in the embodiment, as will be described below in Example 1, among the above-described four stages, two stages of non-cancer cell and low grade dysplasia (LGD), which can be easily identified, are roughly classified with high accuracy.

The unsupervised learning is not limited to the cluster analysis, and can appropriately adopt any method as long as it can roughly classify the altered state of the biological tissue. In addition, the categorization by the altered state classification unit 56 narrows down an identification target by being performed before identification by the altered state identification unit 57 and improves identification accuracy and versatility, but does not necessarily need to be executed. Further, in the case of analyzing the canceration state in the polyp, there is no stage of non-cancer cell, and therefore the categorization by the altered state classification unit 56 is not necessary.

The altered state identification unit 57 categorizes the pixels corresponding to the analysis target region with the supervised learning to identify the altered state of the biological tissue. In the embodiment, the altered state identification unit 57 adopts logistic regression having a high categorization function as supervised learning. Therefore, as will be described below in Example 3, two stages of high grade dysplasia (HGD) and cancer cell, which are difficult to identify in the altered state classification unit 56, are also identified with high accuracy.

The supervised learning is not limited to the logistic regression, and can appropriately adopt Neural network-related techniques including support vector machine (SVM), random forest, and deep learning, and discriminant analysis as long as it can identify the altered state of the biological tissue. In addition, when the non-cancer cell and the low grade dysplasia (LGD) are not roughly classified in advance by the altered state classification unit 56, the altered state identification unit 57 may directly identify each of the four stages. Further, when only the categorization by the altered state classification unit 56 is sufficient, the identification by the altered state identification unit 57 is not necessary to be executed.

Next, operations of the biological tissue analyzing device 1, the biological tissue analyzing program 1a, and the biological tissue analyzing method of the embodiment will be described.

In the case of analyzing the altered state of the biological tissue using the biological tissue analyzing device 1, the biological tissue analyzing program 1a, and the biological tissue analyzing method of the embodiment, first, the hyperspectral data acquisition unit 51 acquires hyperspectral data of the biological tissue from the hyperspectral camera 10 (step S1: hyperspectral data acquisition step) as shown in FIG. 4.

At this time, a visible light source is used, which has a higher transparency of a microscope lens compared with infrared rays or ultraviolet rays and is less susceptible to aberrations, in the embodiment. In addition, visible light has less influence on the human body than X-rays, and its optical spectrums has potentially containing information on many cell tissues. Therefore, hyperspectral data suitable for analyzing the altered state of the biological tissue is acquired.

Next, the analysis target region extraction unit 52 extracts pixels corresponding to the analysis target region from the two-dimensional image of the biological tissue based on the hyperspectral data acquired by the hyperspectral data acquisition unit 51 (step S2: analysis target region extraction step). Thus, since the spectral information of the pixel is output as data for analysis, the data for analysis is processed according to an analysis mode (step S3).

Specifically, when a high-accuracy mode is set (step S3: YES), the light source effect removal unit 53 divides the spectral information of each pixel corresponding to the analysis target region by the spectral information of the light source (step S4: light source effect removal step). Thus, since the effect of the light source on the data for analysis is removed, analysis accuracy is improved.

Subsequently, the staining effect removal unit 54 removes the spectral component that changes depending on the staining density of the analysis target region (step S5: staining effect removal step). Thus, since the effect of staining on the data for analysis is removed, analysis accuracy is improved.

On the other hand, when the high-accuracy mode is not set (step S3: NO), the data quantity reduction unit 55 reduces the number of data for analysis (step S6: data quantity reduction step). Thus, an analysis speed is improved in a state where the analysis accuracy is constant as will be described below in Example 2.

After the processing according to the analysis mode is executed, the altered state classification unit 56 categorizes each of the pixels corresponding to the analysis target region with unsupervised learning (step S7: altered state classification step). Thus, since the altered state of the biological tissue is roughly classified and the target to be identified by the altered state identification unit 57 is narrowed down, analysis accuracy is improved.

Subsequently, the altered state identification unit 57 categorizes each of the pixels corresponding to the analysis target region with supervised learning (step S8: altered state identification step). Thus, the altered state of the biological tissue is identified with high accuracy. In the embodiment, the analysis result is displayed on the display means 2 according to a ratio of the number of pixels categorized in each of the altered states to the total number of pixels (step S9: analysis result display step).

In the embodiment, steps S1 and S2 described above may be executed by an analysis device (program) separate from the biological tissue analyzing device 1. In other words, the hyperspectral data of the biological tissue is acquired from the hyperspectral camera 10 by the separate analysis device, and the pixels corresponding to the analysis target region are extracted based on the hyperspectral data. Then, the pixels may be acquired and analyzed by the biological tissue analyzing device 1.

In addition, steps S3 to S6 and S9 described above are not essential processes, but are processes that are appropriately executed as necessary or according to selection of the user. Further, one or both of steps S7 and S8 described above are executed according to the required analysis accuracy, and the analysis accuracy is improved in the order of only step S7, only step S8, and both steps S7 and S8.

According to the biological tissue analyzing device 1, the biological tissue analyzing program 1a, and the biological tissue analyzing method of the embodiment as described above, the following effects can be obtained.

1. The altered state of the biological tissue can be identified with high accuracy using the hyperspectral data.
2. The effect of the light source on the data for analysis can be removed, and the analysis accuracy can be improved.
3. The effect of staining on the data for analysis can be removed, and the analysis accuracy can be improved.
4. The analysis target region can be extracted in pixel units.
5. The analysis target region can be extracted in cell nucleus units.
6. The canceration state of the cell nucleus in the ulcer or the polyp can be identified according to pathological diagnosis.
7. The visible light can be included in the wavelength band, and the hyperspectral data suitable for analyzing the altered state of the biological tissue can be acquired.

Specific examples of the biological tissue analyzing device 1, the biological tissue analyzing program 1a, and the biological tissue analyzing method according to the present invention will be described below.

Example 1

In Example 1, an experiment was performed to confirm identification performance of the cluster analysis adopted as the unsupervised learning by the altered state classification unit 56 in the above-described embodiment.

Specifically, first, a specimen related to ulcerative colitis was prepared as a biological tissue, and a pathologist identified four stages of non-cancer cell, low grade dysplasia (LGD), high grade dysplasia (HGD), and cancer cell in advance. Next, hyperspectral data of the cell nucleus was acquired for each of the four identified stages.

In Example 1, the hyperspectral data was acquired by directly bringing the hyperspectral camera 10 (Hokkaido Satellite Co., Ltd.: HSC1702) into contact with an eyepiece of an upright microscope (Olympus Corporation). At this time, a white LED built into the microscope was used as a light source, and the microscope had a magnification of 400 times (with an eyepiece having a magnification of 10 times and an objective having a magnification of 40 times). In addition, a measurement wavelength range was visible light from 350 nm to 1050 nm and a near infrared range, and hyperspectral data of a total of 141 bands was acquired with a wavelength sampling interval of 5 nm.

Next, the acquired hyperspectral data was subjected to cluster analysis by the Ward method, and three or four feature quantities were extracted as clusters. Then, an identification rate (similarity) of all the feature quantities extracted for each stage was calculated by main component analysis and linear discriminant analysis, and the presence or absence of the feature quantity serving as an index of each stage was examined. The result is shown in FIG. 5.

As shown in FIG. 5, non-cancers 1 to 4, which are the feature quantities of non-cancer cells, had an identification rate of almost 100% with respect to other feature quantities. Accordingly, it was shown that the non-cancer cells could be easily identified by cluster analysis. In addition, an LGD1, which is one of the feature quantities of the low grade dysplasia (LGD), was 83.3% or more in identification with respect to other feature quantities, and was about 95.5% on average. Therefore, it was shown that the low grade dysplasia (LGD) had a unique feature quantity that the cancer cell and the high grade dysplasia (HGD) did not have, and that the low grade dysplasia (LGD) could be identified from other stages by cluster analysis using such a feature quantity.

According to Example 1 described above, it was shown that the cluster analysis as unsupervised learning could identify the non-cancer cell and the low grade dysplasia (LGD), among the four stages in the canceration state of the ulcer, with high accuracy.

Example 2

In Example 2, an experiment was performed to confirm performance of the main component analysis adopted as the data quantity reduction method by the data quantity reduction unit 55 in the above-described embodiment.

Specifically, first, samples of cancer cells and high grade dysplasia (HGD) were prepared which were difficult to identify by the cluster analysis, and hyperspectral data was acquired by the same method as in Example 1. Next, the number of hyperspectral data was reduced to two-dimensional data by main component analysis, and a contribution rate was calculated. The result is shown in FIG. 6. As shown in FIG. 6, since a cumulative contribution rate from a first main component to a second main component exceeds 90%, it was shown that the loss of information quantity was extremely small even when a dimension up to a third main component was reduced.

According to Example 2 described above, it was shown that the main component analysis can reduce the number of data with almost no loss of the information quantity of the hyperspectral data and can improve an analysis speed.

Example 3

In Example 3, an experiment was performed to confirm identification performance of the logistic regression adopted as the supervised learning by the altered state identification unit 57 in the above-described embodiment.

Specifically, first, the hyperspectral data of the cancer cells and high grade dysplasia (HGD) whose number of data was reduced in Example 2 was prepared. Next, using a Logistic Regression function in an extension module (scikit-learn) of numerical analysis software (Python), analysis was performed by logistic regression. At this time, training data and test data were divided at a ratio of 7:3 in a state where a ratio of the number of high grade dysplasia (HGD) samples (490 samples) and the number of cancer cell samples (320 samples) is maintained, learning and prediction (identification) were performed, and the identification rate was as high as 95.9%.

In addition, regarding the prediction result, a confusion matrix showing the number of true positives, false positives, false negatives, and true negatives is shown in FIG. 7. An F-value (a harmonic mean of accuracy and recall), which is one of rating scales of the prediction result, was calculated based on the confusion matrix shown in FIG. 7, the value being a high score of 96.9%. In addition, each numerical value in the matrix shows the following value.

Upper left (true positive: TP): cancer, and cells identified as cancer

Upper right (false positive: FP): HGD, but cells identified as cancer

Lower left (false negative: FN): cancer, but cells identified as HGD

Lower right (true negative: TN): HGD, and cells identified as HGD

According to Example 3 described above, it was shown that the logistic regression as supervised learning can identify the cancer cells and the high grade dysplasia (HGD), among the four stages in the canceration state of the ulcer, with high accuracy.

Example 4

In Example 4, an experiment was performed to compare analysis accuracy when analysis was performed by a support vector machine which is one of supervised learning with analysis accuracy when an analysis target was narrowed down in advance by cluster analysis which is one of unsupervised learning and then analysis was performed by a support vector machine.

Specifically, a specimen related to ulcerative colitis was prepared, and in the ulcer, four stages of non-cancer cell, low grade dysplasia (LGD), high grade dysplasia (HGD), and cancer cell were identified only by a support vector machine. Further, for the same specimen, after non-cancer cell was previously identified by the cluster analysis, the remaining three stages of low grade dysplasia (LGD), high grade dysplasia (HGD), and cancer cell were identified by the support vector machine. The result is shown in FIG. 8.

As shown in FIG. 8(a), when the analysis was performed only by the support vector machine, identification rates of the four stages of cancer cell, low grade dysplasia (LGD), high grade dysplasia (HGD), and non-cancer cell were 92.2%, 78.8%, 55.6%, and 100.0%, respectively. On the other hand, as shown in FIG. 8(b), when analysis was performed by a combination of the cluster analysis and the support vector machine, identification rates of the three stages of cancer cell, low grade dysplasia (LGD), and high grade dysplasia (HGD) were 90.0%, 71.0%, and 86.6%, respectively.

In other words, when the analysis was performed by the combination of the cluster analysis and the support vector machine, the identification rate of low grade dysplasia (LGD) was improved by 7.8%, and the identification rate of high grade dysplasia (HGD) was improved by 15.4%.

According to Example 4 described above, it was shown that the identification of the canceration state of the ulcer is more accurate when the altered state classification unit 56 identified the canceration state by the combination of the unsupervised learning and the supervised learning compared with when the altered state identification unit 57 identified the canceration state only by the supervised learning.

Example 5

In Example 5, an experiment was performed to specify a spectral component that should be removed by the staining effect removal unit 54 and that changes depending on the staining density of the analysis target region in the above-described embodiment.

Specifically, first, a paraffin-embedded slice was prepared from a surface epithelial tumor of cancer fixed with formalin and was subjected to hematoxylin-eosin staining to prepare a pathological specimen. In the hematoxylin-eosin staining, chromatin in the nucleus is stained in a deep blue-purple color. For this reason, light transmittance changes depending on a chromatic concentration in the cell nucleus, and a spectral change depending on an absorption spectrum of a staining solution is observed.

Next, using the hyperspectral camera 10 as in Example 1, the magnification was fixed at 200 times and three hyperspectral images were taken from one specimen on average. In the cancer cell, the cell nucleus is enlarged and confirmation of cytoplasm is difficult. Therefore, ten cell nuclei were analyzed from one hyperspectral image, and an average spectrum for each cell nucleus was used.

Subsequently, staining densities in the hyperspectral image were visually divided into three levels, and staining levels were set to staining level 1, staining level 2, and staining level 3 in order of low staining density. Then, the number of independent components was set to three, and independent component analysis of hyperspectral data was performed. The result is shown in FIG. 9. In the analysis, reflection intensity measured by dividing a wavelength range from 445 nm to 745 nm into 5 nm bands was used.

As shown in FIG. 9, it was confirmed that the independent component indicated by Signal1, among three independent components (Signal1, Signal2, and Signal3), changed stepwise in the wavelength range of 540 nm to 700 nm. On the other hand, it was confirmed that the other independent components (Signal2 and Signal3) were almost common in all the staining levels. Therefore, it can be said that the independent component indicated by Signal1 is a spectral component that changes depending on the staining density.

According to Example 5 described above, it was shown that the spectral component which changes depending on the staining density of the analysis target region, can be extracted by the independent component analysis of the hyperspectral data.

The biological tissue analyzing device 1, the biological tissue analyzing program 1a, and the biological tissue analyzing method according to the present invention are not limited to the above-described embodiment, and can be changed as appropriate.

For example, the cluster analysis is adopted as the unsupervised learning by the altered state classification unit 56 in the above-described embodiment, but is not limited thereto. For example, main component analysis may be adopted as the unsupervised learning, and the hyperspectral data whose dimensions have been reduced by the main component analysis may be analyzed by linear discriminant analysis.

In addition, the canceration state of the cell nucleus in the ulcer or the polyp is identified as the altered state of the biological tissue in the above-described embodiment, but, specifically, the altered state of the biological tissue to be described below can be identified.

(1) Among pancreatic duct epithelial cells: normal cells, acinar cell carcinoma of pancreatic body (ACC), neuroendocrine tumor (NET), solid pseudopapillary neoplasm (SPN), and pancreatic cancer cells (2) Among prostate cells: atrophic cells, prostate cancer cells, and prostatic hyperplasia cells (3) Among uterine cells: low grade dysplasia (CIN1), middle grade dysplasia (CIN2), and high grade dysplasia/carcinoma in situ (CIN3)

(4) Among lung cells: squamous-cell carcinoma and adenocarcinoma (5) Among ductal cells: three grades of invasive ductal carcinoma and three grades of non-invasive ductal carcinoma Further, the data quantity reduction unit 55 reduces the dimension of the data for analysis with the main component analysis in the above-described embodiment, but an auto encoder, which is an algorithm for dimension compression using a neural network, may be used without being limited to such a method. Alternatively, a plurality of clusters may be formed using cluster analysis, which is one of unsupervised learning, as preprocessing of supervised data and analysis target data, and a part of the clusters may be removed as noise clusters.

Further, the hematoxylin-eosin staining is performed at the time of measurement of the biological tissue in the above-described embodiment, but immunostaining used for visualizing an antigen-antibody reaction (immune reaction) may be used as long as it has identifiability at the cell level without being limited thereto.

Further, the hyperspectral camera 10 is brought into contact with the eyepiece of the microscope to measure the biological tissue in the above-described embodiment, but the hyperspectral camera 10 may be brought into contact with an eyepiece of a trinocular microscope to measure the biological tissue without being limited to such a configuration.

REFERENCE SIGNS LIST

1 biological tissue analyzing device
1a biological tissue analyzing program
2 display means
3 input means
4 storage means
5 arithmetic processing means
10 hyperspectral camera
41 program storage unit
42 supervised data storage unit
51 hyperspectral data acquisition unit
52 analysis target region extraction unit
53 light source effect removal unit
54 staining effect removal unit
55 data quantity reduction unit
56 altered state classification unit
57 altered state identification unit

The invention claimed is:

1. A biological tissue analyzing device configured to analyze a biological tissue using hyperspectral data in which spectral information is associated with each of pixels forming a two-dimensional image and comprising the following (i) and (ii), as well as comprising (iii) and/or (iv):
   (i) a hyperspectral data acquisition unit configured to acquire the hyperspectral data of the biological tissue from a hyperspectral camera;
   (ii) an analysis target region extraction unit configured to extract, based on the hyperspectral data, pixels corresponding to an analysis target region from a two-dimensional image of the biological tissue by image processing;
   (iii) an altered state classification unit configured to roughly classify an altered state of the biological tissue by categorizing the pixels corresponding to the analysis target region with unsupervised learning; and
   (iv) an altered state identification unit configured to identify the altered state of the biological tissue by categorizing the pixels corresponding to the analysis target region with supervised learning
   wherein the biological tissue analyzing device further comprises a light source effect removal unit configured to divide the spectral information of the pixels corresponding to the analysis target region by spectral information of a light source used at the time of acquisition of the hyperspectral data.

2. A biological tissue analyzing device configured to analyze a biological tissue using hyperspectral data in which spectral information is associated with each of pixels forming a two-dimensional image and comprising the following (i) and (ii), as well as comprising (iii) and/or (iv):
   (i) a hyperspectral data acquisition unit configured to acquire the hyperspectral data of the biological tissue from a hyperspectral camera;
   (ii) an analysis target region extraction unit configured to extract, based on the hyperspectral data, pixels corresponding to an analysis target region from a two-dimensional image of the biological tissue by image processing;
   (iii) an altered state classification unit configured to roughly classify an altered state of the biological tissue by categorizing the pixels corresponding to the analysis target region with unsupervised learning; and
   (iv) an altered state identification unit configured to identify the altered state of the biological tissue by categorizing the pixels corresponding to the analysis target region with supervised learning,
   wherein the biological tissue analyzing device further comprises a staining effect removal unit configured to remove a spectral component which changes depending on staining density of the analysis target region, based on the spectral information of the pixels corresponding to the analysis target region.

3. A biological tissue analyzing device configured to analyze a biological tissue using hyperspectral data in which spectral information is associated with each of pixels forming a two-dimensional image and comprising the following (i) and (ii), as well as comprising (iii) and/or (iv):
- (i) a hyperspectral data acquisition unit configured to acquire the hyperspectral data of the biological tissue from a hyperspectral camera;
- (ii) an analysis target region extraction unit configured to extract, based on the hyperspectral data, pixels corresponding to an analysis target region from a two-dimensional image of the biological tissue by image processing;
- (iii) an altered state classification unit configured to roughly classify an altered state of the biological tissue by categorizing the pixels corresponding to the analysis target region with unsupervised learning; and
- (iv) an altered state identification unit configured to identify the altered state of the biological tissue by categorizing the pixels corresponding to the analysis target region with supervised learning, wherein the analysis target region extraction unit labels on each of the pixels as the analysis target region or other regions based on similarity of the spectral information, and performs filtering on the pixel labeled as the analysis target region.

4. A biological tissue analyzing device configured to analyze a biological tissue using hyperspectral data in which spectral information is associated with each of pixels forming a two-dimensional image and comprising the following (i) and (ii), as well as comprising (iii) and/or (iv):
- (i) a hyperspectral data acquisition unit configured to acquire the hyperspectral data of the biological tissue from a hyperspectral camera;
- (ii) an analysis target region extraction unit configured to extract, based on the hyperspectral data, pixels corresponding to an analysis target region from a two-dimensional image of the biological tissue by image processing;
- (iii) an altered state classification unit configured to roughly classify an altered state of the biological tissue by categorizing the pixels corresponding to the analysis target region with unsupervised learning; and
- (iv) an altered state identification unit configured to identify the altered state of the biological tissue by categorizing the pixels corresponding to the analysis target region with supervised learning, wherein the analysis target region extraction unit performs image recognition processing on the two-dimensional image of the biological tissue to specify a glandular duct, and specifies a cell nucleus present on the glandular duct, as an analysis target region, by image recognition processing.

5. A biological tissue analyzing device configured to analyze a biological tissue using hyperspectral data in which spectral information is associated with each of pixels forming a two-dimensional image and comprising the following (i) and (ii), as well as comprising (iii) and/or (iv):
- (i) a hyperspectral data acquisition unit configured to acquire the hyperspectral data of the biological tissue from a hyperspectral camera;
- (ii) an analysis target region extraction unit configured to extract, based on the hyperspectral data, pixels corresponding to an analysis target region from a two-dimensional image of the biological tissue by image processing;
- (iii) an altered state classification unit configured to roughly classify an altered state of the biological tissue by categorizing the pixels corresponding to the analysis target region with unsupervised learning; and
- (iv) an altered state identification unit configured to identify the altered state of the biological tissue by categorizing the pixels corresponding to the analysis target region with supervised learning, wherein the altered state specified by the altered state classification unit is, in an ulcer: two stages of non-cancer cell and low grade dysplasia (LGD), and the altered state identified by the altered state identification unit is, in the ulcer: four stages of non-cancer cell, low grade dysplasia (LGD), high grade dysplasia (HGD), and cancer cell, or, in a polyp: three stages of low grade adenoma (LGA), high grade adenoma (HGA), and cancer cell.

6. The biological tissue analyzing device according to claim 1, wherein visible light is included in a wavelength band of the hyperspectral data.

7. A non-transitory computer-readable recording medium storing a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):
- (i) a hyperspectral data acquisition unit configured to acquire the hyperspectral data of the biological tissue from a hyperspectral camera;
- (ii) an analysis target region extraction unit configured to extract, based on the hyperspectral data, pixels corresponding to an analysis target region from a two-dimensional image of the biological tissue by image processing;
- (iii) an altered state classification unit configured to roughly classify an altered state of the biological tissue by categorizing the pixels corresponding to the analysis target region with unsupervised learning; and
- (iv) an altered state identification unit configured to identify the altered state of the biological tissue by categorizing the pixels corresponding to the analysis target region with supervised learning, wherein the computer is caused to further function as a light source effect removal unit configured to divide the spectral information of the pixels corresponding to the analysis target region by spectral information of a light source used at the time of acquisition of the hyperspectral data.

8. A non-transitory computer-readable recording medium storing a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):
- (i) a hyperspectral data acquisition unit configured to acquire the hyperspectral data of the biological tissue from a hyperspectral camera;
- (ii) an analysis target region extraction unit configured to extract, based on the hyperspectral data, pixels corresponding to an analysis target region from a two-dimensional image of the biological tissue by image processing;
- (iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning, wherein the computer is caused to further function as a staining effect removal unit configured to remove a spectral component which changes depending on staining density of the analysis target region, based on the spectral information of the pixels corresponding to the analysis target region.

9. A non-transitory computer-readable recording medium storing a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):

(i) a hyperspectral data acquisition unit configured to acquire the hyperspectral data of the biological tissue from a hyperspectral camera;

(ii) an analysis target region extraction unit configured to extract, based on the hyperspectral data, pixels corresponding to an analysis target region from a two-dimensional image of the biological tissue by image processing;

(iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning, wherein the analysis target region extraction unit labels on each of the pixels as the analysis target region or other regions based on similarity of the spectral information, and performs filtering on the pixel labeled as the analysis target region.

10. A non-transitory computer-readable recording medium storing a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):

(i) a hyperspectral data acquisition unit configured to acquire the hyperspectral data of the biological tissue from a hyperspectral camera;

(ii) an analysis target region extraction unit configured to extract, based on the hyperspectral data, pixels corresponding to an analysis target region from a two-dimensional image of the biological tissue by image processing;

(iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning, wherein the analysis target region extraction unit performs image recognition processing on the two-dimensional image of the biological tissue to specify a glandular duct, and specifies a cell nucleus present on the glandular duct, as an analysis target region, by image recognition processing.

11. A non-transitory computer-readable recording medium storing a biological tissue analyzing program configured to analyze a biological tissue using hyperspectral data in which spectral information is associated with each of pixels forming a two-dimensional image and causing a computer to function as the following (i) and (ii), as well as causing the computer to function as (iii) and/or (iv):

(i) a hyperspectral data acquisition unit configured to acquire the hyperspectral data of the biological tissue from a hyperspectral camera;

(ii) an analysis target region extraction unit configured to extract, based on the hyperspectral data, pixels corresponding to an analysis target region from a two-dimensional image of the biological tissue by image processing;

(iii) an altered state classification unit configured to roughly classify an altered state of the biological tissue by categorizing the pixels corresponding to the analysis target region with unsupervised learning; and (iv) an altered state identification unit configured to identify the altered state of the biological tissue by categorizing the pixels corresponding to the analysis target region with supervised learning, wherein the altered state specified by the altered state classification unit is, in an ulcer: two stages of non-cancer cell and low grade dysplasia (LGD), and the altered state identified by the altered state identification unit is, in the ulcer: four stages of non-cancer cell, low grade dysplasia (LGD), high grade dysplasia (HGD), and cancer cell, or, in a polyp: three stages of low grade adenoma (LGA), high grade adenoma (HGA), and cancer cell.

12. A biological tissue analyzing method of analyzing a biological tissue using hyperspectral data in which spectral information is associated with each of pixels forming a two-dimensional image and comprising the following (i) and (ii), as well as comprising (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue, wherein the biological tissue analyzing method further comprises a light source effect removal step of dividing the spectral information of the pixels corresponding to the analysis target region by spectral information of a light source used at the time of acquisition of the hyperspectral data.

13. A biological tissue analyzing method of analyzing a biological tissue using hyperspectral data in which spectral information is associated with each of pixels forming a two-dimensional image and comprising the following (i) and (ii), as well as comprising (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue, wherein the biological tissue analyzing method further comprises a staining effect removal step of removing a spectral component which changes depending on staining density of the analysis target region, based on the spectral information of the pixels corresponding to the analysis target region.

14. A biological tissue analyzing method of analyzing a biological tissue using hyperspectral data in which spectral information is associated with each of pixels forming a two-dimensional image and comprising the following (i) and (ii), as well as comprising (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue, wherein in the analysis target region extraction step, each of the pixels is labeled as the analysis target region or other regions based on similarity of the spectral information, and filtering is performed on the pixel labeled as the analysis target region.

15. A biological tissue analyzing method of analyzing a biological tissue using hyperspectral data in which spectral information is associated with each of pixels forming a two-dimensional image and comprising the following (i) and (ii), as well as comprising (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue, wherein in the analysis target region extraction step, image recognition processing is performed on the two-dimensional image of the biological tissue to specify a glandular duct, and a cell nucleus present on the glandular duct is specified, as an analysis target region, by image recognition processing.

16. A biological tissue analyzing method of analyzing a biological tissue using hyperspectral data in which spectral information is associated with each of pixels forming a two-dimensional image and comprising the following (i) and (ii), as well as comprising (iii) and/or (iv):

(i) a hyperspectral data acquisition step of acquiring the hyperspectral data of the biological tissue from a hyperspectral camera;

(ii) an analysis target region extraction step of extracting, based on the hyperspectral data, pixels corresponding to an analysis target region from a two-dimensional image of the biological tissue by image processing;

(iii) an altered state classification step of categorizing the pixels corresponding to the analysis target region with unsupervised learning to roughly classify an altered state of the biological tissue; and (iv) an altered state identification step of categorizing the pixels corresponding to the analysis target region with supervised learning to identify the altered state of the biological tissue, wherein the altered state specified in the altered state classification step is, in an ulcer: two stages of non-cancer cell and low grade dysplasia (LGD), and the altered state identified by the altered state identification step is, in the ulcer: four stages of non-cancer cell, low grade dysplasia (LGD), high grade dysplasia (HGD), and cancer cell, or, in a polyp: three stages of low grade adenoma (LGA), high grade adenoma (HGA), and cancer cell.

* * * * *